(12) United States Patent
Suen et al.

(10) Patent No.: US 7,282,596 B2
(45) Date of Patent: Oct. 16, 2007

(54) METHOD AND INTERMEDIATE FOR PREPARING A PROSTAGLANDIN F-TYPE COMPOUND

(75) Inventors: Rung-Tian Suen, Taipei (TW); Yu-Liang Liu, Taipei (TW)

(73) Assignee: Everlight USA, Inc., Pineville, NC (US)

( * ) Notice: Subject to any disclaimer, the term of this patent is extended or adjusted under 35 U.S.C. 154(b) by 108 days.

(21) Appl. No.: 11/102,839

(22) Filed: Apr. 11, 2005

(65) Prior Publication Data

US 2006/0079693 A1    Apr. 13, 2006

(30) Foreign Application Priority Data

Oct. 10, 2004  (CN)  .................. 2004 1 0085224

(51) Int. Cl.
*C07D 307/935* (2006.01)
(52) U.S. Cl. ........................................ 549/305; 560/61
(58) Field of Classification Search ................ 549/305; 560/61
See application file for complete search history.

(56) References Cited

U.S. PATENT DOCUMENTS

2003/0149294 A1    8/2003    Gutman et al. ............... 560/55

*Primary Examiner*—Taofiq Solola
(74) *Attorney, Agent, or Firm*—Bacon & Thomas PLLC

(57) ABSTRACT

A method for preparing a prostaglandin F-type compound. Also disclosed is an intermediate of the following formula (II) compound

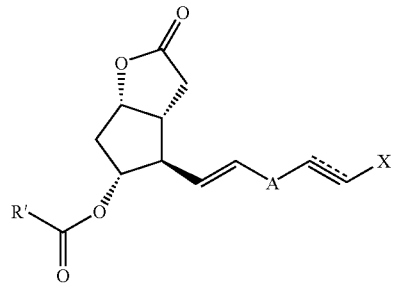

wherein R', X and A have the same meaning as given in the specification.

19 Claims, No Drawings

METHOD AND INTERMEDIATE FOR PREPARING A PROSTAGLANDIN F-TYPE COMPOUND

BACKGROUND OF THE INVENTION

1. Field of the Invention

The present invention relates to a method for preparing a prostaglandin F-type compound, and an intermediate for preparing the prostaglandin F-type compound.

2. Description of the Related Prior Art

The derivatives of prostaglandin F-type are capable using in clinical treatments for glaucoma or high intraocular pressure caused by other reasons. Glaucoma is a disease caused by a continued or intermittent high intraocular pressure. The continued high pressure will bring damage to eyeball tissues and vision ability, if it didn't serve treatment in time, it will also bring damage to optic nerve system and lead to vision recession or narrowed eyesight. The most serious situation is losing vision. Presently, glaucoma is one of the three critical diseases causing blind. The derivatives of prostaglandin F-type show good curative effect in treating glaucoma and high intraocular pressure that caused by other reasons. Therefore, the using and preparing method of prostaglandin F-type compound now become a main focus for many chemists and pharmacists. Some prior arts were disclosed in U.S. Pat. No. 4,599,353, Europe patent No. 364,417, No. 495069, No. 544,899, PCT publication No. WO95/11003, WO01/055101, WO01/087816, WO02/096868, WO02/096898, and WO03/008368.

SUMMARY OF THE INVENTION

The present invention provides a prepared method of the prostaglandin F-type compound. The present invention also provides an intermediate for preparing the prostaglandin F-type compound.

The method of the present invention includes steps of preparing a compound of the following formula (I):

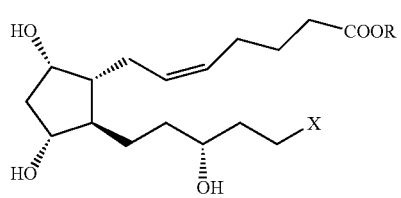

wherein

R is hydrogen or $C_1$-$C_5$ alkyl;

X is $C_1$-$C_6$ alkyl, thiazol, imidazole, pyrrolidine, thiophene, oxazole or a phenyl group with 0 to 3 substituted groups, wherein said substituted groups are selected from the group consisting of $C_1$-$C_5$ alkyl, $C_1$-$C_4$ alkoxy, trifluoromethyl group, $C_1$-$C_3$ aliphatic acylamino group, nitro group, halogen atom, and phenyl group.

The compound of the formula (I) is made by a synthesized reaction of the following intermediate formula (II):

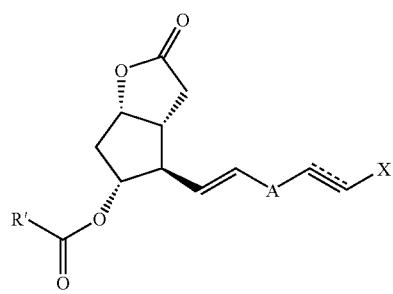

wherein

X is defined the same as above formula (I);

R' is a $C_1$-$C_6$ aryl group with 0 to 3 substituted groups, wherein said the substituted groups are the group consisting of halogen, $C_1$-$C_6$ alkyl, or $C_6$-$C_{10}$ aryl;

A is C=O or C—OH;

≡≡≡ is a triple bond or a double bond in the cis or trans configuration.

When A is a bivalent of CH(OH) group, the intermediate is as the following formula (II-b):

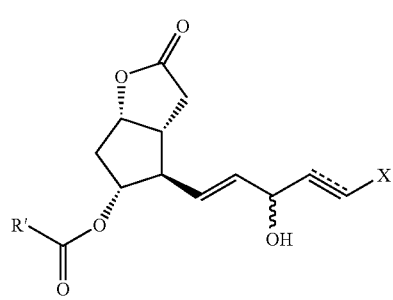

wherein R', X and ≡≡≡ are defined the same as the above formula (II) compound.

The formula (I) compound of the present invention can be prepared by Protected-Corey aldelyde as shown below

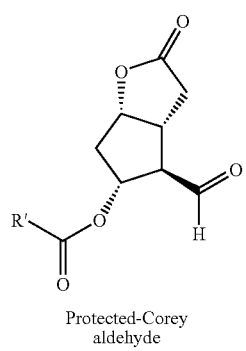

Protected-Corey aldehyde wherein R' is defined as the above formula (II) compound; with a Phosphonate compound as shown below

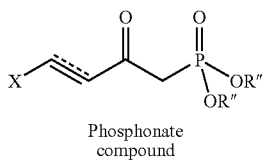

Phosphonate compound wherein R'' is $C_1-C_6$ alkyl; X and ═══ are defined the same as the above formula (II) compound for reacting (such as Witting Reaction) to form the following formula (II-a) compound:

(II-a)

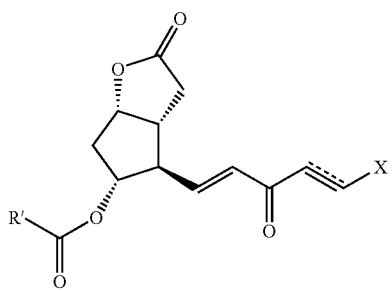

wherein R', X and ═══ are defined the same as the formula (II) compound.

The intermediate of the following formula (II-b) compound (II-b)

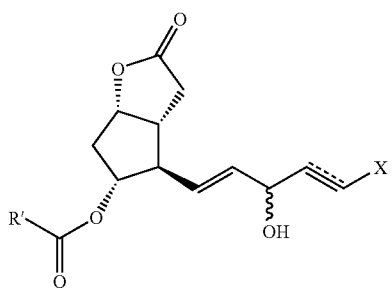

wherein R', X and ═══ are defined as the above formula (II) compound; can be obtained by reducing the formula (II-a) compound.

Separating the formula (II-b) compound to obtain the following formula (S)-(II-b) compound and formula (R)-(II-b) compound (S)-(II-b)

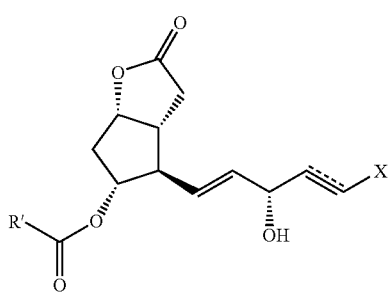

(R)-(II-b)

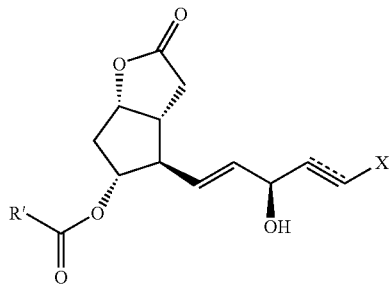

wherein R', X and ═══ are defined as above.

The formula (S)-(II-b) compound is undergo a hydrogenation reaction to form the following formula (III) compound (III)

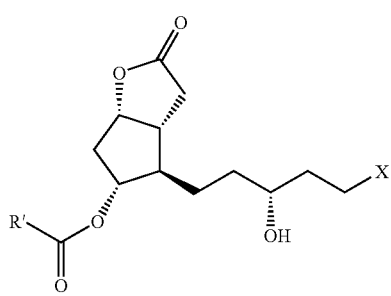

wherein R' and X are defined as the formula (II) compound.

After deprotecting the formula (III) compound, a compound of the following formula (IV) can be obtained, (IV)

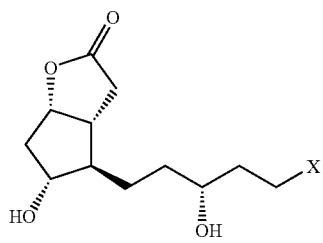

wherein X is defined as the formula (II) compound.

Besides, there are other methods for preparing formula (IV) compound, for example, proceeding a deprotection reaction for the formula (S)-(II-b) compound to obtain the following intermediate (S)-(II-c)

(S)-(II-c)

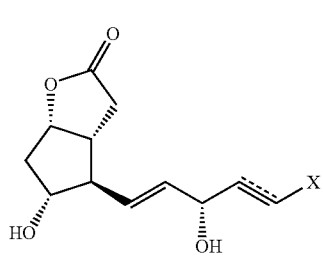

wherein X and ═══ are defined as the above formula (II) compound; then hydrogenating the formula (S)-(II-c) compound to form the formula (IV) compound, reacting the hydroxyl group of formula (IV) compound with protection reagent to form the following formula (V) compound

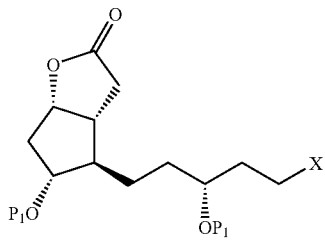

(V)

wherein X is defined as the above formula (II) compound; $P_1$ is a hydroxyl-protecting group selected from the group consistin of N,N'-Bis(trimethylsilyl)urea, trimethylsilyl, triethylsilyl, t-butyldimethylsilyl, t-butyldiphenylsilyl, phenyldimethylsilyl, and tetrahydrofuranyl.

Reducing the lactone oxo group to lactol group of the intermediate formula (V) compound to obtain the following formula (VI) compound

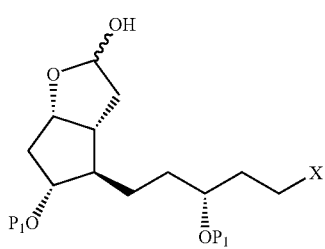

(VI)

wherein X and $P_1$ are defined as the above formula (V) compound.

Reacting formula (VI) compound with the following formula (α) compound

(α)

wherein $R^a$ is $C_1$-$C_6$ alkyl or $C_6$-$C_{10}$ aryl group; Y is fluoro, chloro, bromo or iodo; to form the following formula (VII) compound

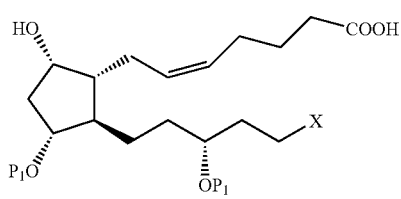

(VII)

wherein X and $P_1$ are defined as the above formula (V) compound.

Reacting the formula (VII) compound and the following formula compound

R—Z wherein R is defined as the above formula (I) compound; Z is halogen, sulphate, mesyl, or tosyl; to form the following formula (VIII) compound

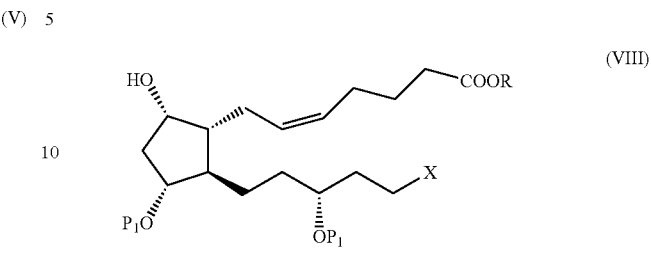

(VIII)

wherein X and $P_1$ are defined the same as the above formula (V) compound; R is defined the same as the above formula (I) compound; deprotecting the formula (VIII) compound under the acid condition to obtain the prostaglandin F-type compound of formula (I) compound.

DETAILED DESCRIPTION OF THE PREFERRED EMBODIMENTS

The present invention relates to a method for preparing the following formula (I) compound:

wherein R is hydrogen or $C_1$-$C_5$ alkyl; X is $C_1$-$C_6$ alkyl, thiazol, imidazole, pyrrolidine, thiophene, oxazole or a phenyl group with 0 to 3 substituted groups, wherein said substituted groups are selected from the groups consisting of $C_1$-$C_5$ alkyl, $C_1$-$C_4$ alkoxy, trifluoromethyl group, $C_1$-$C_3$ aliphatic acylamino group, nitro group, halogen atom, and phenyl group; using the intermediate as the following formula (II) compound (II)

wherein R', X and ═══ are defined as above mentioned; A is C═O or C—OH; to process a synthesis reaction, when A is a C═O group, the intermediate is as following formula (II-a)

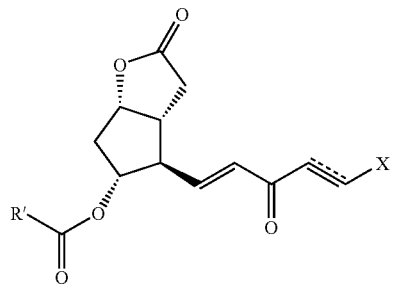

(II-a)

wherein R', X and ═══ are defined as above; when A is a C—OH group, the intermediate is as following formula (II-b)

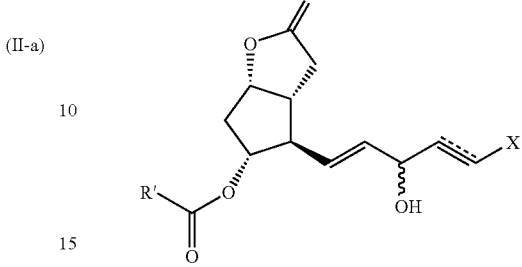

(II-b)

wherein R', X and ═══ are defined the same as above mentioned. The concrete synthesis process of formula (I) compound of the present invention is as the following Reaction Scheme 1.

Reaction Scheme 1

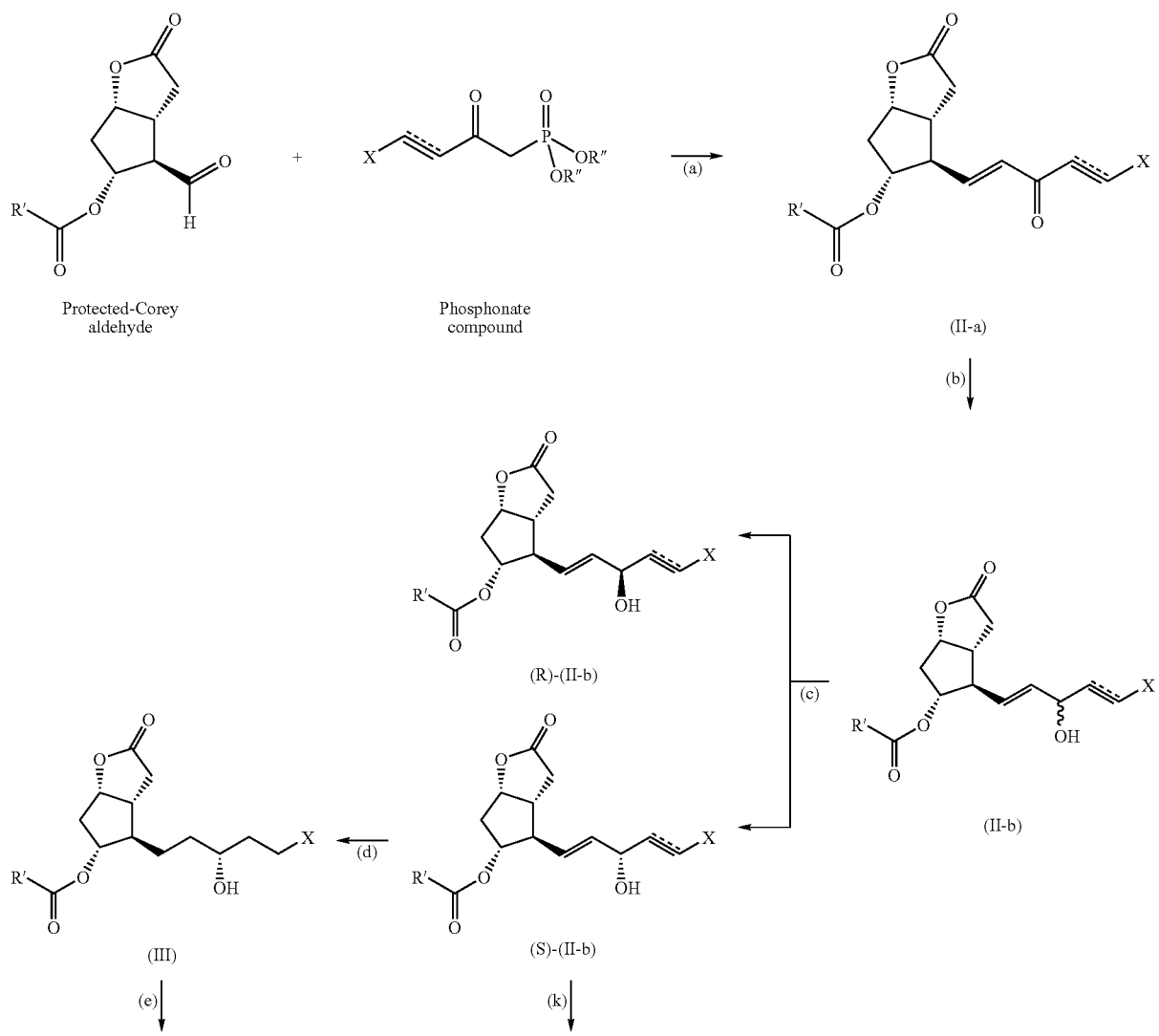

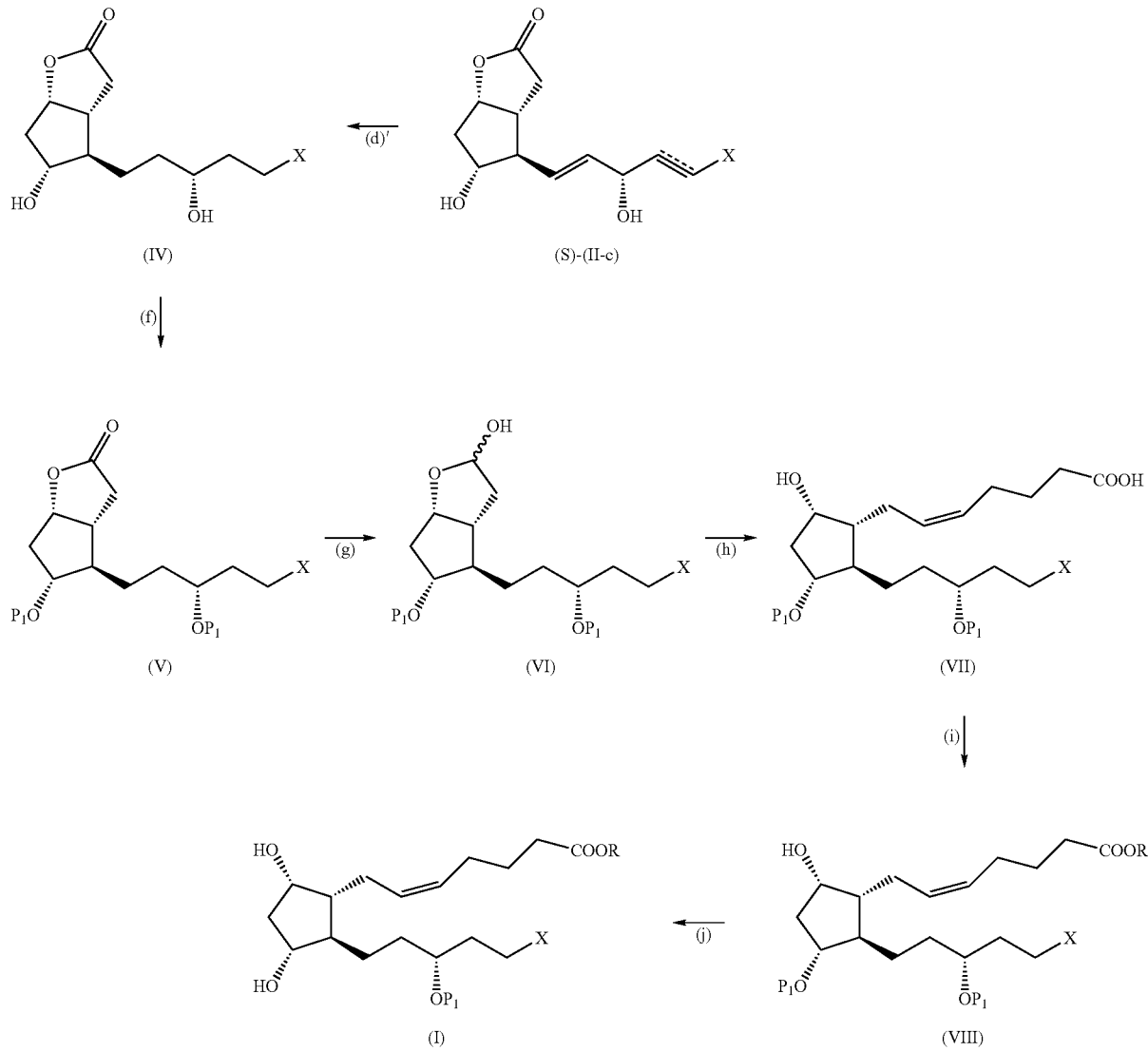

The preparation of the following formula (II-a) compound of the present invention

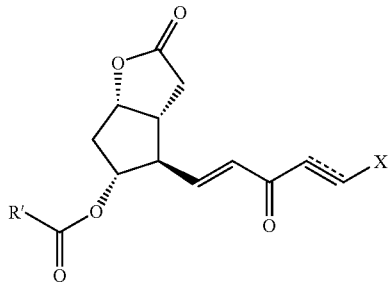

wherein R' is an aryl group with 0 to 3 substituted groups, wherein said substituted group are selected from the groups consisting of halogen atom, $C_1$-$C_6$ alkyl, or $C_6$-$C_{10}$ aryl group; X and ⇌ are defined the same as above mentioned; is as the step (a) of the Reaction Scheme 1, reacting (such as Wittig Reaction) the following Protected-Corey aldehyde

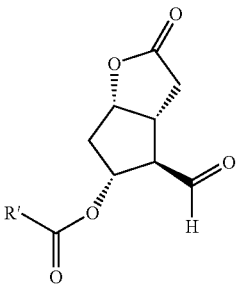

Protected-Corey aldehyde wherein R' defined the same as above mentioned; with the following phosphonate compound

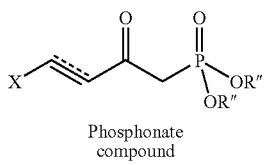

Phosphonate compound wherein R" is $C_1$-$C_6$ alkyl; X and ≡≡≡ are defined the same as above; to form the formula (II-a) compound.

The preparation process is to reacting the Protected-Corey aldehyde and the phosphonate compound in the organic solvent with the alkaline reagent to form the formula (II-a) compound.

The above organic solvent can be selected from the group consisting of high-polar organic solvent, medium-polar organic solvent, and chlorinated solvent. Examples of the above organic solvent are THF, toluene, methylene chloride, dichloroethane, or ether. It is preferred that said organic solvent are THF or toluene, and more preferably is THF.

The alkaline reagents using in the reaction comprise organic or inorganic alkali. For examples, triethylamine, diisopropylethylamine, 1,8-diazabicyclo(5.4.0)undec-7-ene (DBU), sodium hydride (NaH), or potassium carbonate. It is preferred are triethylamine, diisopropylethylamine, 1,8-diazabicyclo(5.4.0)undec-7-ene or sodium hydride (NaH), and more preferably are triethylamine, or diisopropylethylamine.

General speaking, the range of the reaction temperature is between –20° C. to 40° C., preferably between –10° C.~30° C.

The preparation of the formula (II-b) compound of the present invention

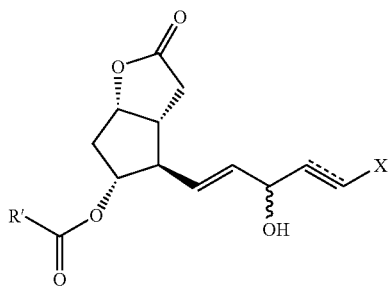

(II-b)

wherein R', X and ≡≡≡ are defined the same as above-mentioned; is as the step (b) of the Reaction Scheme 1, reducing the formula (II-a) compound

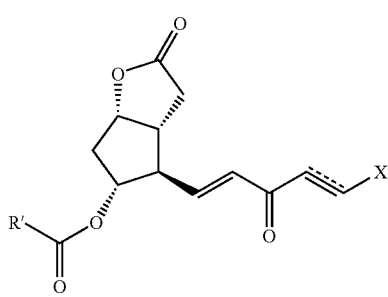

(II-a)

wherein R', X and ≡≡≡ are defined the same as above; with side chain carbonyl.

Reducing the formula (II-a) compound with appropriate reducing agent, wherein the reducing agent is the general agent to reduce the ketone group to hydroxyl group. Examples of the above reducing agent are borane-dimethylsulfide complex (Corey-catalyst), lithium aluminum hydride (LAH), sodium borohydride (NaBH$_4$), lithium tri-sec-butylborohydride, or binaphthol-EtOH-LAH complex (Nouryi-Catalyst). Lithium aluminum hydride (LAH) or binaphthol-EtOH-LAH complex (Nouryi-Catalyst) are preferable.

The reaction temperature depends on the reducing agent used in the reaction. It could be range from 30° C. to –100° C. For instance, when using the lithium aluminum hydride (LAH), the reaction temperature is between –60° C. to –70° C., and the reaction temperature is between 30° C. to 0° C. while using the sodium borohydride (NaBH$_4$).

In the present invention, reducing the formula (II-a) compound to get the formula (II-b) compound, then separating the formula (II-b) compound as the step (c) of the Reaction Scheme 1 to obtain the following formula (S)-(II-b) and (R)-(II-b)

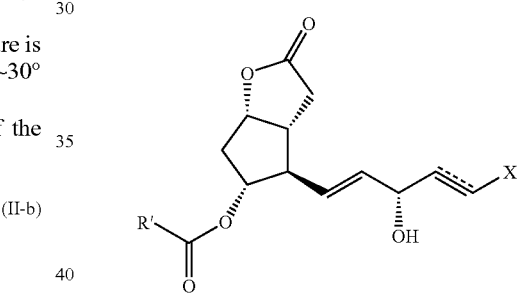

(S)-(II-b)

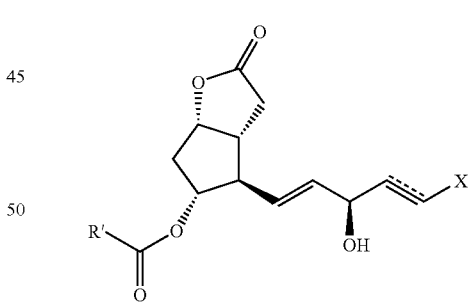

(R)-(II-b)

wherein R', X and ≡≡≡ are defined the same as above mentioned; the isolation process of formula (II-b) comprise column chromatography, the stuffing using in the column, for example, Silica gel or Aluminum oxide, both can be used for isolation.

The mobile phase using in the isolation process will be some general polar organic solvents, for example, ester, ether, alcohol, alkane group solvents or its mixed solvents, the preferred solvents among are ethyl acetate, ethyl ether, isopropyl ketone, hexane, heptane or its mixed solvents.

The following formula (S)-(II-b) compound of the present invention

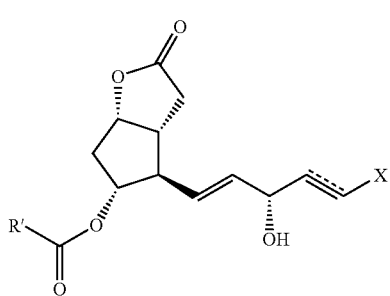

(S)-(II-b)

wherein R', X and ⁼⁼⁼⁼ are defined the same as the above; could be reacted as in the step (d) of the Reaction Scheme 1. Hydrogenating the (S)-(II-b) compound with metal catalyst and hydrogen in the organic solvent to form the following formula (III) compound

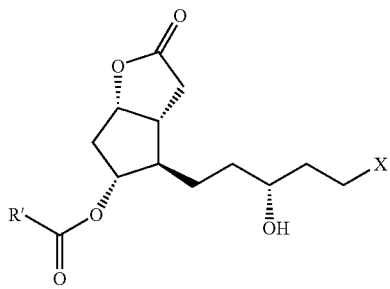

(III)

wherein R' and X are defined the same as above mentioned; Examples of the organic solvent used in the hydrogenation reaction are methanol, ethanol, isopropyl alcohol, ethyl acetate, THF, or toluene. It is preferred that said organic solvent are methanol, THF, or ethyl acetate, and more preferably is methanol.

Examples of metal catalysts used in the hydrogenation reaction are raney nickel, rhodium, ruthenium, iridium, platinum, palladium, wherein platinum or palladium is preferably, and palladium is the most preferred.

The range of temperature for the hydrogenation reaction of the present invention can be from 0° C. to 40° C., it depends on what kind of solvents used in the reaction. The reaction time is also not strictly limited, it is preferred that said reaction time is 1 hour to 2 hours.

The formula (III) compound of the present invention can be further proceed as the step (e) of the Reaction Scheme 1, such as deprotecting the following formula (III) compound

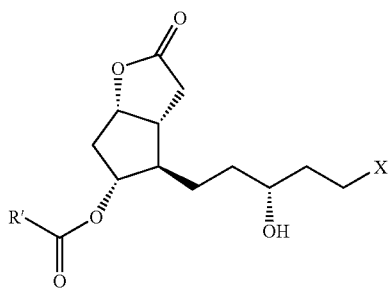

(III)

wherein R' and X are defined the same as above; with the alkaline reagent in the organic solvent to form the following formula (IV) compound

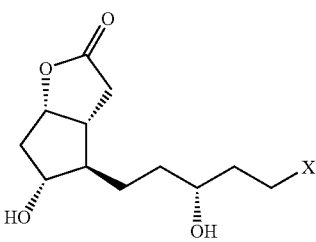

(IV)

wherein X is defined the same as above. Examples of the organic solvent used in the above reaction are methanol, ethanol, isopropyl alcohol, ethyl acetate, THF, or toluene. It is preferred that said organic solvent are methanol, ethanol, or isopropyl alcohol, and more preferably is methanol.

The alkaline reagent used in the deprotection reaction will deprotect the —COR' to form the hydroxyl group. Examples of the alkaline reagent are potassium carbonate, lithium carbonate, sodium hydroxide, or potassium hydroxide. It is preferred that said alkaline reagent are potassium carbonate, or potassium hydroxide, and most preferably is potassium hydroxide.

The range of the reaction temperature can be from 30° C. to –5° C., it depends on what kind of alkaline reagent used in the reaction.

There are other methods to obtain the formula (IV) compound of the present invention. Take the step (k) of the Reaction Scheme 1 for example, to deprotect the formula (S)-(II-b) compound with the alkaline reagent in the organic solvent to form the following formula (S)-(II-c)

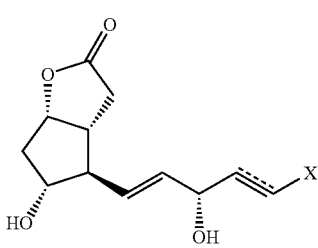

(S)-(II-c)

wherein X and ⁼⁼⁼⁼ are defined the same as above; the organic solvent, alkaline reagent and the reaction temperature are the same as those of the deprotection reaction mentioned in the step (e) of the Reaction Scheme 1, then further proceeding the formula (S)-(II-c) compound as the step (d)' of the Reaction Scheme 1. Hydrogenating the formula (S)-(II-c) compound with the metal catalysts and hydrogen in the organic solvent to form the formula (IV) compound. The condition of the organic solvent, the metal catalysts and the reaction temperature of the hydrogenation reaction are the same as that of the step (d) in the Reaction Scheme 1.

The formula (IV) compound of the present invention can be further proceeding as the step (f) of the Reaction Scheme 1. Proceeding the following formula (IV) compound

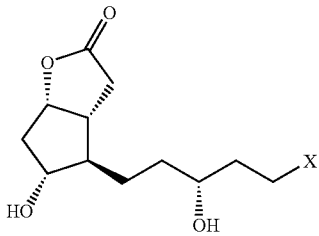
(IV)

wherein X is defined the same as above; with acid condition protection reaction or alkaline condition protection reaction in the organic solvent. The process of the above reaction is to add the acid or alkaline catalyst, and then the protecting reagent to form the following formula (v) compound

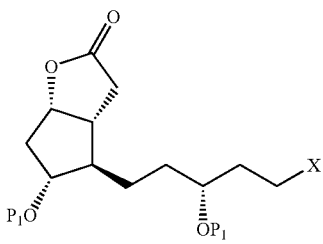
(V)

wherein $P_1$ is a hydroxyl-protecting group, said hydroxyl-protecting group is selected from the group consisting of: N,N'-Bis(trimethylsilyl)urea, trimethylsilyl, triethylsilyl, tbutyldimethylsilyl, t-butyldiphenylsilyl, phenyldimethylsilyl, or tetrahydrofuranyl; X is defined the same as above. The organic solvent of the said reaction is the normal polar solvent such as THF, DMF, DMSO, toluene, ether, dichloromethane, or dichloroethane. It is preferred to use the medium-polar or high-polar solvent such THF, DMF, toluene, or ether.

The catalyst is organic alkali and organic acid such as triethylamine, diisopropylethylamine, pyridinium p-toluenesulfonate (PPTS), p-toluenesulfonic acid (PTSA), or 1,8-diazabicyclo(5.4.0)undec-7-ene (DBU), wherein triethylamine, pyridinium p-toluenesulfonate (PPTS), or p-toluenesulfonic acid (PTSA) are preferred.

The protecting reagent of the said reaction are N,N'-Bis(trimethylsilyl)urea, trimethylsilyl chloride, triethylsilyl chloride, tert-butyldimethylsilyl chloride, t-butyldiphenylsilyl, phenyldimethylsilyl chloride, or dihydropyran (DHP), wherein the trimethylsilyl chloride, triethylsilyl chloride, or dihydropyran (DHP) are preferred.

The reaction temperature ranges from 30° C. to −10° C., and more preferably is from 0° C. to −5° C.

The formula (V) compound of the present invention can be further proceeding as the step (g) of the Reaction Scheme 1. Reducing the formula (V) compound

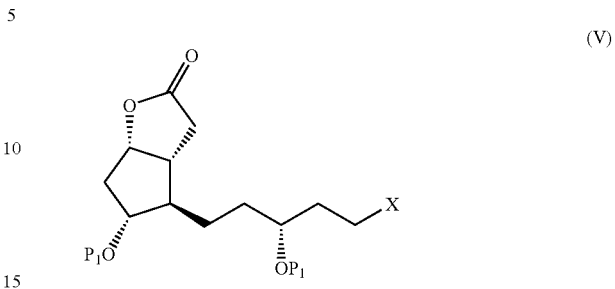
(V)

wherein X and $P_1$ are defined the same as above; with reducing reagent under low temperature in the presence of the organic solvent. Reducing the lactone oxo group into lactol group to form the following formula (VI) compound

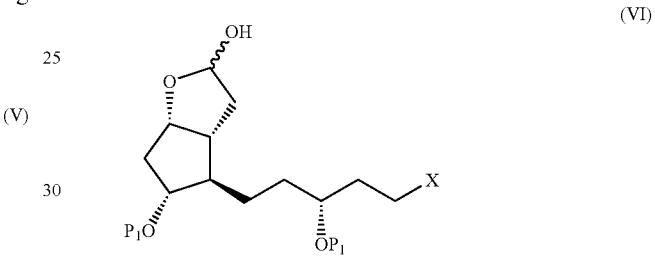
(VI)

wherein $P_1$ and X are defined the same as above. The organic solvent of the said reaction are normal polar solvent such as THF, toluene, ether, methylene chloride, or dichloroethane. It is preferred that said solvent is THF, toluene, or ether, and more preferably are THF or toluene.

The example of the reducing reagent is di-iso-butyl aluminum hydride (DIBAL-H). The reaction temperature ranges from −60° C. to −80° C., and reaction temperature from −60° C. to −70° C. is preferred. Further proceeding the formula (VI) compound with the following formula (α) compound

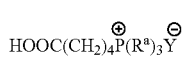
(α)

wherein $R^a$ is $C_1$-$C_6$ alkyl or $C_6$-$C_{10}$ aryl group; Y is fluoro, chloro, bromo or iodo; as the reaction (such as Witting Reaction) in the step (h) of the Reaction Scheme 1 to form the following formula (VII) compound

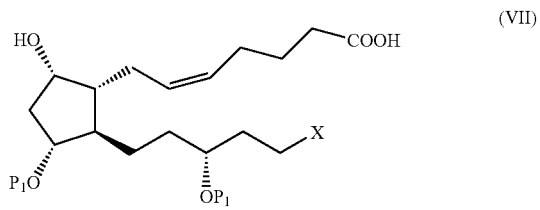
(VII)

wherein X and $P_1$ are defined the same as above; further reacting the carboxylic acid of formula (VII) compound to ester group with esterification, such as reacting the formula (VII) compound with the following formula (β) compound

R—Z    (β)

wherein R is defined the same as above; Z is halogen, sulphate, mesyl, or tosyl; to form the following formula (VIII) compound

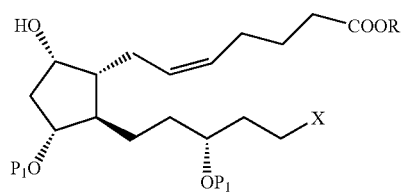
(VIII)

wherein X, R and $P_1$ are defined the same as above; deprotecting the formula (VIII) compound under acid condition to obtain the crude product of the formula (I) compound. We obtain formula (I) prostaglandin F-type compound after purified the crude products of formula compound (I) with general column chromatography.

The formula (V) compound/the formula (VI) compound obtained by the Reaction Scheme I of the present invention is a known prostaglandin intermediate. The said intermediate can be further synthesize by the method described in the European Patent No. 495069 and Zhongguo Yaowu Huaxue Zazhi (1998), 8(3), 213-217, to form the following formula (I) compound

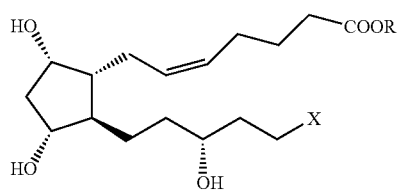
(I)

wherein X and R are defined the same as above. The synthesis method of the prostaglandin in the said references is as the following Reaction Scheme 2.

Reaction Scheme 2

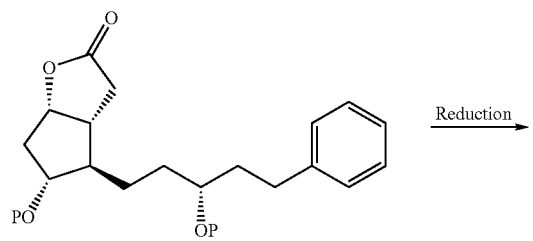
Reduction →

-continued

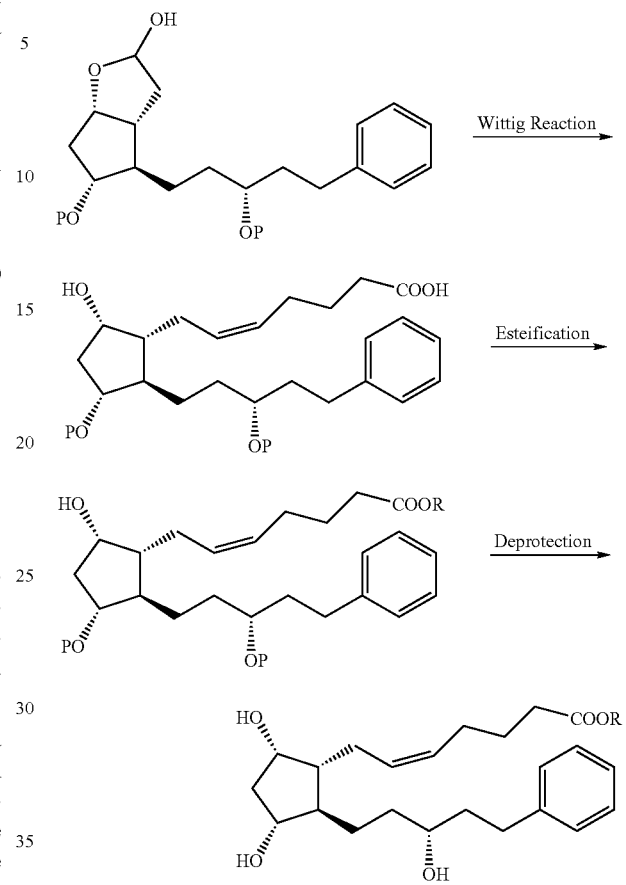

wherein P is the protection group. The characteristic of the present invention is providing an intermediate to prepare the prostaglandin F-type compound. The said intermediate includes formula (II-a) compound

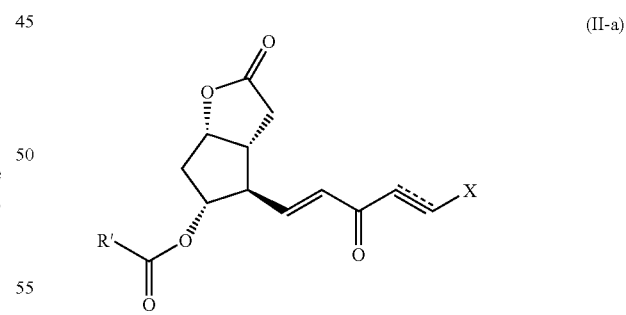
(II-a)

wherein R' is a aryl group with 0 to 3 substituted groups, wherein said substituted groups are selected from the groups consisting of halogen atom, $C_1$-$C_6$ alkyl, or $C_6$-$C_{10}$ aryl group; X is $C_1$-$C_6$ alkyl, thiazol, imidazole, pyrrolidine, thiophene, oxazole or a phenyl group with 0 to 3 substituted groups, wherein said substituted groups are selected from the groups consisting of $C_1$-$C_5$ alkyl, $C_1$-$C_4$ alkoxy, trifluoromethyl group, $C_1$-$C_3$ aliphatic acylamino group, nitro group, halogen atom, and phenyl group; ≡≡≡is a triple bond or a double bond in the cis or trans configuration; formula (II-b) compound

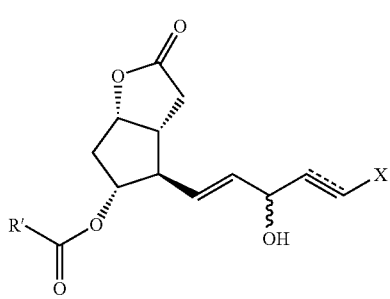

wherein R', X and ═══ are defined the same as above; formula (S)-(II-b) compound

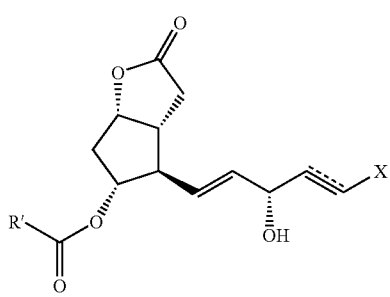

wherein R', X and ═══ are defined the same as above; formula (R)-(II-b) compound

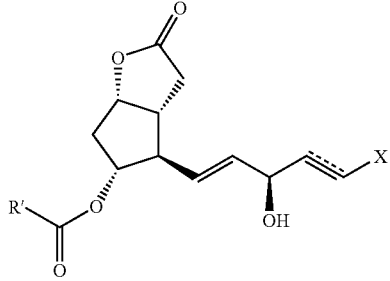

wherein R', X and ═══ are defined the same as above; and the formula (S)-(II-c) compound

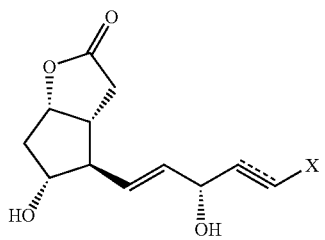

wherein X and ═══ are defined the same as above;

More detailed examples are used to illustrate the present invention, and these examples are used to explain the present invention. The examples below, which are given simply by way of illustration, must not be taken to limit the scope of the invention. Any skilled personnel in the field can simply modify or amend the invention and it is all included in the following area. Unless specifically specify, the examples are in weight percent, and temperature unit is in degree Celsius ° C.

EXAMPLE 1

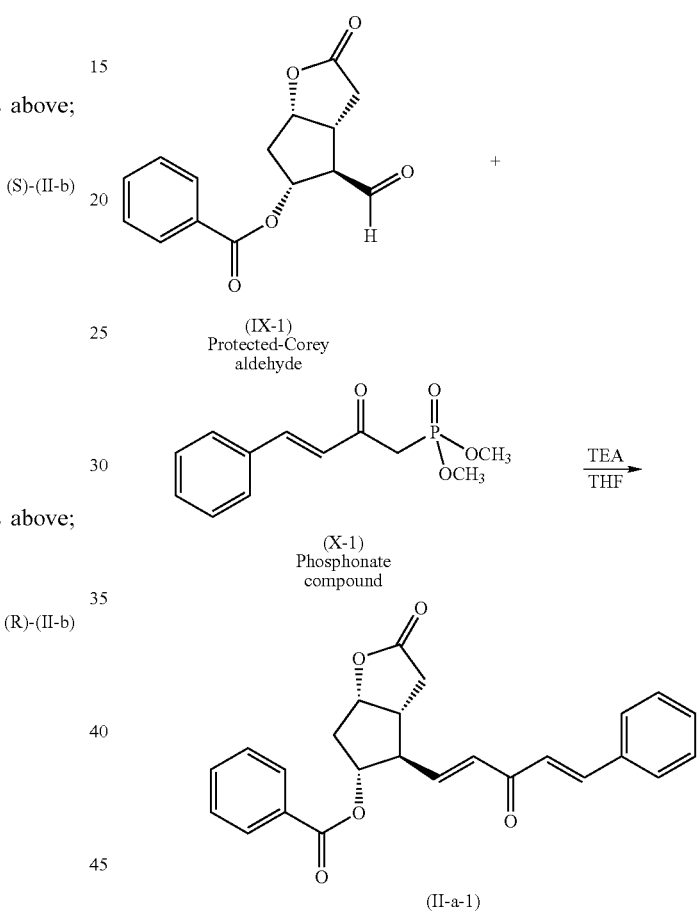

Formula (IX-1) compound (1.65 g) and THF (25 ml) were added into a 100 ml three-neck bottle. The temperature of the reaction solution was cooled to 0~5° C., then a mixed solution of formula (X-1) compound and THF (1.7 g of formula (X-1) compound in 12.5 ml of THF) was added and stirred for 30 minutes. A mixed solution of triethyl amine and THF (0.67 g TEA in 10 ml THF) was added into the above solution and stirred for 1.0 hour. After the reaction was completed, the reaction solution was filtered with a G3 filter plate. The filtrate was concentrated for a yellow oil (2.0 g), then purified the yellow oil with column chromatography for the formula (II-a-1)1.0 g。

$^1$H NMR (CDCl$_3$):

δ: 8.12-7.92(d, 2H), 7.78-7.32(m, 9H), 6.98-6.82(d, 2H), 6.68-6.55 (d, 1H), 5.42-5.30(q, 1H), 5.19-5.08(m, 1H), 3.05-2.82(m, 3H), 2.73-2.42 (m, 2H), 2.36-2.25 (dd, 1H)

$^{13}$C NMR (CDCl$_3$):

δ: 188.22, 176.01, 165.90, 144.06, 143.60, 134.20, 133.28, 130.58, 130.06, 129.84, 129.47, 129.07, 128.78, 128.36, 128.26, 128.22, 124.71, 83.21, 78.57, 54.13, 42.52, 37.66, 34.78

MS: m/z=403 (M+H), m/z=425 (M+Na)

EXAMPLE 2

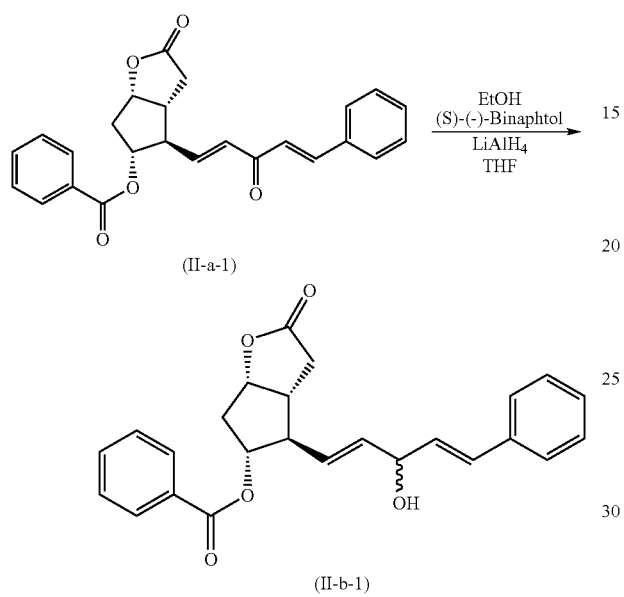

Add 1.37 ml (1.37 mmole) LiAlH$_4$ into 50 ml three-necked bottle then decrease the temperature to 0~5° C., add 0.057 g EtOH dissolve in 5 ml THF then add dropwise into the reaction bottle, stir for half an hour, then dissolve 0.36 g (S)-(−)-Binaphthol in 5 ml THF, add and stir into the reaction bottle, decrease the temperature to −70~−80° C. then add the mixture of compound (II-a-1) and THF solution (0.5 g compound (II-a-1) dissolve in 5 ml THF solution), and stir for 2 hours, add 10 ml ethyl acetate and 10 ml NH$_4$Cl saturated solution, then extract with 50 ml ethyl acetate, obtain the solution from upper layer, concentrated to give 0.2 g oil-residue.

$^1$H NMR (CDCl$_3$):

δ: 8.20-7.90(m, 2H), 7.59-7.43(m, 1H), 7.42-7.37(m, 2H), 7.18-7.36 (m, 5H), 6.60-6.51 (d, 1H), 6.20-6.05 (dd, 1H), 5.82-5.60 (m, 2H), 5.35-5.20 (q, 1H), 5.09-4.98 (m, 1H), 4.82-4.72 (t, 1H), 2.93-2.72 (m, 3H), 2.65-2.43 (m, 2H), 2.30-2.15 (dd, 1H)

$^{13}$C NMR (CDCl$_3$):

δ: 176.4, 166.02, 136.22, 134.23, 133.29, 131.13, 129.97, 129.59, 129.44, 128.93, 128.54, 128.48, 127.88, 126.49, 83.25, 79.01, 72.75

MS: m/z=427 (M+Na)

EXAMPLE 3

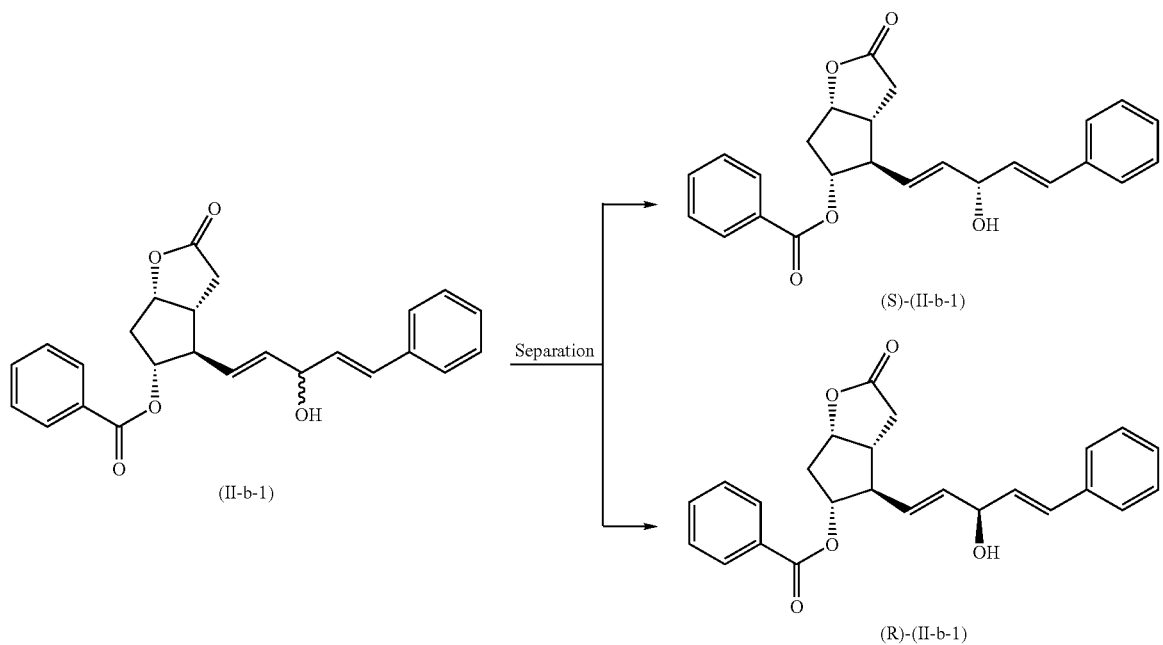

Column: 40 mm diameter, 7.5 cm Length

Stuffing: Silica gel (200-230 mesh)

Flowing rate: 18 ml/min

Collecting: 20 ml per bottle

Dissolving 1.3 g (II-b-1) in 1 ml ethyl acetate then loading into the column, wash with EA/Hexane: 1/1, collecting 20 ml for each tube, then testing result with TLC, collecting two compounds; Rf=0.35 and Rf=0.30, analysis the compounds with NMR and HPLC, the result shows below:

1. Compound (S)-(II-b-1)

(1) HPLC result:

(S)-(II-b-1)/(R)-(I-b-1)=99.73/0.27(area %)

(2) $^1$H NMR (CDCl$_3$):

δ: 8.06-7.93 (d, 2H), 7.60-7.52 (t, 1H), 7.50-7.38 (t, 2H), 7.37-7.21 (m, 5H), 6.61-6.50 (d, 1H), 6.20-6.05 (dd, 1H), 5.82-5.62 (m, 2H), 5.31-5.20 (q, 1H), 5.12-5.00 (t, 1H), 4.82-4.75 (t, 1H), 2.90-2.72 (m, 3H), 2.65-2.45 (m, 2H), 2.30-2.19 (dd, 1H)

$^{13}$C NMR (CDCl$_3$):

δ: 176.39, 166.03, 136.22, 134.23, 133.29, 131.13, 129.97, 129.59, 129.44, 128.93, 128.54, 128.48, 127.88, 126.49, 83.26, 79.03, 72.71, 54.06, 42.61, 37.52, 34.91

(3) $[\alpha]_D^{25}$=−86.94 (C=1.0 g/100 ml, Acetonitrile)

2. Compound (R)-(II-b-1)

(1) HPLC result:

(R)-(II-b-1)/(S)-(II-b-1)=98.76/1.24 (area %)

(2) $^1$H NMR (CDCl$_3$):

δ: 8.06-7.93 (d, 2H), 7.60-7.52 (t, 1H), 7.50-7.38 (t, 2H), 6.60-6.50 (d, 1H), 6.20-6.10(dd, 1H), 5.80-5.60(m, 2H), 5.30-5.20(q, 1H), 5.12-5.00 (t, 1H), 4.82-4.70 (t, 1H), 2.90-2.70 (m, 3H), 2.68-2.45 (m, 2H), 2.30-2.18 (dd, 1H)

$^{13}$C NMR (CDCl$_3$):

δ: 176.49, 166.00, 136.24, 134.21, 133.26, 130.78, 130.07, 129.55, 129.38, 129.00, 128.49, 128.43, 127.79, 126.45, 83.29, 79.01, 72.75, 54.04, 42.51, 37.45, 34.90

(3) $[\alpha]_D^{25}$=−66.16 (C=1.0 g/100 ml, Acetonitrile)

EXAMPLE 4

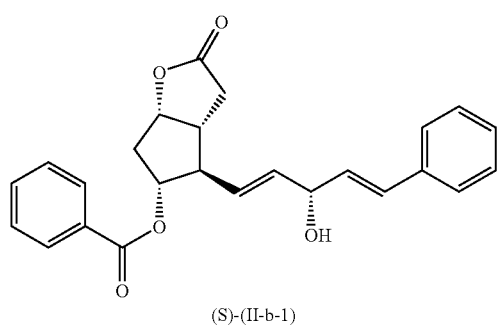

(S)-(II-b-1)

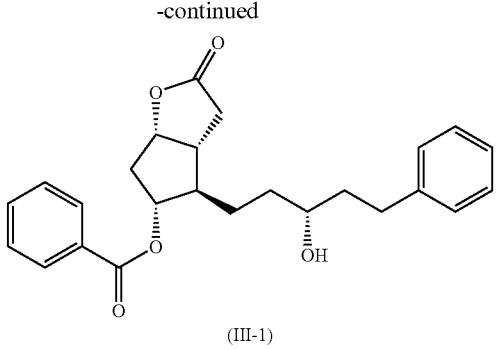

(III-1)

Add 0.2 g compound (S)-(II-b-1), Pd/C 0.01 g and 10 ml methanol into a 25 ml three-necked reaction bottle, stir for 10 mintues then load hydrogen to reaction bottle in 20~25° C., after loading hydrogen, stir for 1.5 hour, analysis with NMR, waiting for the reaction completed, filter with 5 g celite, the filtrate was concentrated, to give 0.17 g light yellow oil-residue.

$^1$H NMR (CDCl$_3$):

δ: 8.10-7.90 (d, 2H), 7.60-7.52 (t, 1H), 7.52-7.39 (t, 2H), 7.37-7.19 (m, 5H), 5.29-5.20 (m, 1H), 5.16-5.04 (m, 1H), 3.72-3.57 (m, 1H)

EXAMPLE 5

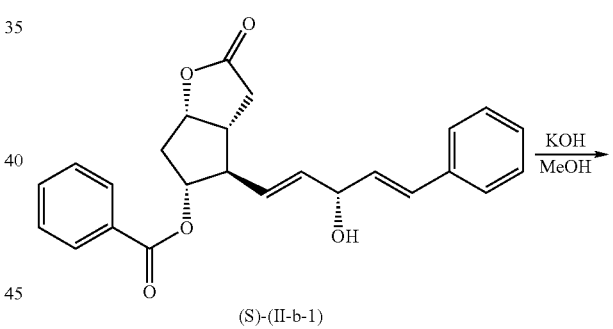

(S)-(II-b-1)

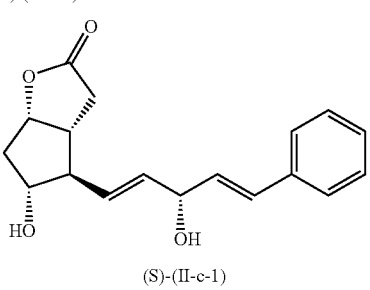

(S)-(II-c-1)

Add 0.14 g compound (S)-(II-b-1), 10 ml methanol and 0.016 g KOH, stir for 2 hours in room temperature, then testing with TLC, waiting for reaction completed, extracted the mixture by adding 9 ml NH$_4$Cl solution, holding until the layers show up, obtain the upper layer, dry with 4 g Na$_2$SO$_4$, then filter the Na$_2$SO$_4$, the filtrate was concentrated to obtain 0.13 g yellow oil-residue, purified by column chromatography, obtain 0.1 g light yellow oil residue.

¹H NMR (CDCl₃):

δ: 7.39-7.21 (m, 5H), 6.61-6.53 (d, 1H), 6.28-6.17(dd, 1H), 5.80-5.45 (m, 2H), 4.89-4.80(m, 1H), 4.79-4.70 (m, 1H), 3.98-3.88(q, 1H), 2.79-2.20 (m, 5H), 1.95-1.90 (m, 1H)

EXAMPLE 6

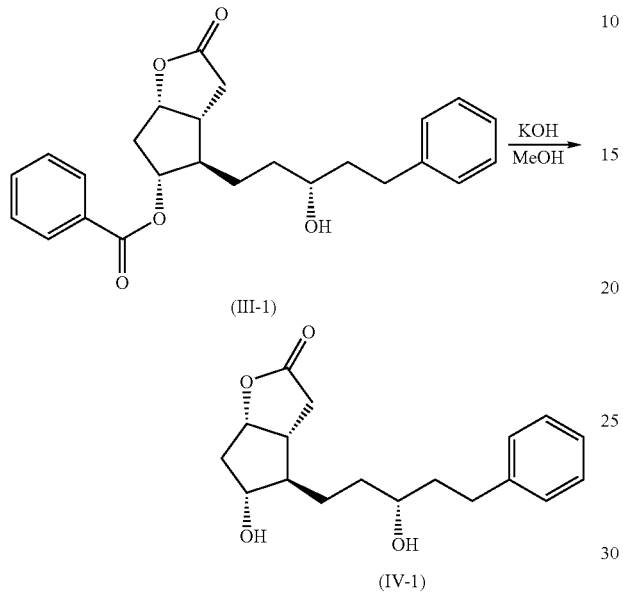

Add 0.17 compound (III-1) and 10 ml methanol into a 25 ml three-necked reaction bottle, stir for 10 minutes, add 0.027 g KOH, sit for 2.5 hours in 20~25° C., analysis with TLC, waiting for reaction complete then extracted by adding 4 g NH₄Cl saturated solution and 20 ml ethyl acetate, wait for forming the layers, obtain the upper layer, dry with Na₂SO₄, filter the Na₂SO₄, concentrated the filtrate obtain 0.16 g yellow residue, obtain 70 mg light yellow oil residue after column chromatography.

¹HNMR (CDCl₃):

δ: 7.32-7.15(m, 5H), 4.93-4.80(m, 1H), 4.00-3.95(q, 1H), 3.63-3.53 (m, 1H), 2.82-2.60 (m, 3H), 2.58-2.46 (m, 2H), 2.36-2.21 (m, 1H), 2.07-1.98 (dd, 1H), 1.89-1.70 (m, 4H), 1.60-1.45 (m, 3H)

¹³C NMR (CDCl₃):

δ: 178.04, 141.87, 128.37, 128.33, 125.82, 84.08, 77.19, 71.16, 53.78, 43.01, 40.21, 39.04, 35.99, 35.15, 31.97, 28.87

EXAMPLE 7

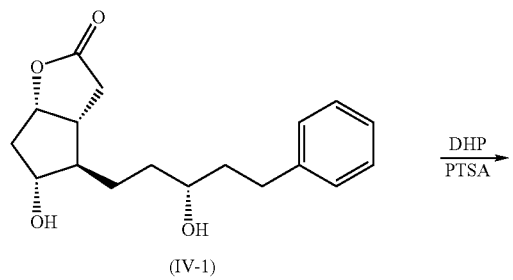

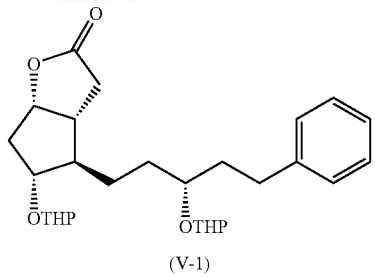

Add 0.7 g compound (IV-1), 15 ml CH₂Cl₂ and 0.043 g (PTSA) into a 50 ml three-necked reaction bottle, in temperature 20~25° C., the DHP solution (dissolve 0.423 g DHP into 5 ml CH₂Cl₂) was added dropwise in nitrogen environment, stir for 2.5 hours then analysis with TLC, wait for the reaction completed, add 5 ml NaHCO₃ and extracted with ethyl acetate, holding still for layers show up, obtain the upper layer, dry with 5 g Na₂SO₄ then filter Na₂SO₄, concentrated the filtrate for 0.9 g yellow oil residue.

¹H NMR (CDCl₃):

δ: 7.35-7.12(m, 5H), 5.01-4.92(q, 1H), 4.70-4.57(m, 2H), 3.98-3.74 (m, 3H), 3.73-3.36(q, 1H), 3.34-3.2(m, 2H), 3.83-2.40(m, 5H), 2.21-2.13 (d, H), 21.90-1.40 (m, 20H)

EXAMPLE 8

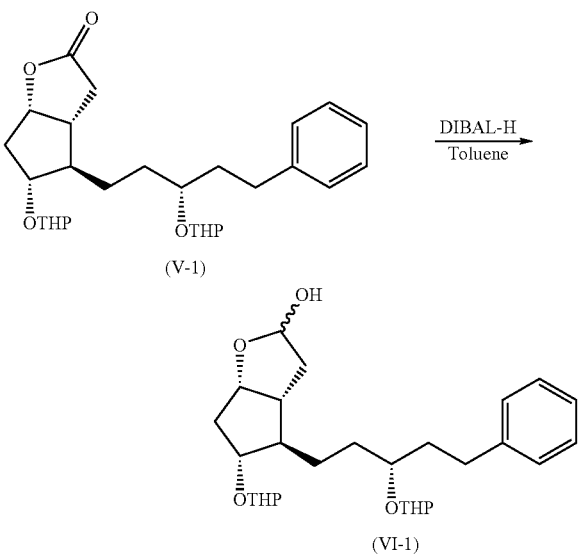

Add 0.9 g compound (V-1) and 15 ml toluene into a 50 ml three-necked reaction bottle, operating in nitrogen environment and decreasing the temperature to −60~−70° C., then 1.42 g (DLBAL-H) (1 M, D=0.7) was added dropwise, stir for 30 minutes and analysis with TLC, wait for reaction completed, remove the dry ice bath, add 15 ml NaHCO₃, stir for 30 minutes, filter with celite, extracted by adding 10 ml water into the filtrate, wait for layers show up, obtain the upper layer, dry with 5 g Na₂SO₄, then filter Na₂SO₄, concentrated the filtrate for 0.9 g yellow oil residue.

¹H NMR (CDCl₃):

δ: 7.31-7.09 (m, 5H), 5.7-5.4 (1H), 4.75-4.57 (m, 3H), 3.98-3.60 (m, 4H), 3.56-3.4(m, 2H), 2.90-2.59(m, 2H), 2.40-2.20(m, 3H), 2.19-2.0 (m, 2H), 1.95-1.40 (m, 20H), 1.40-1.20 (m, 3H)

EXAMPLE 9

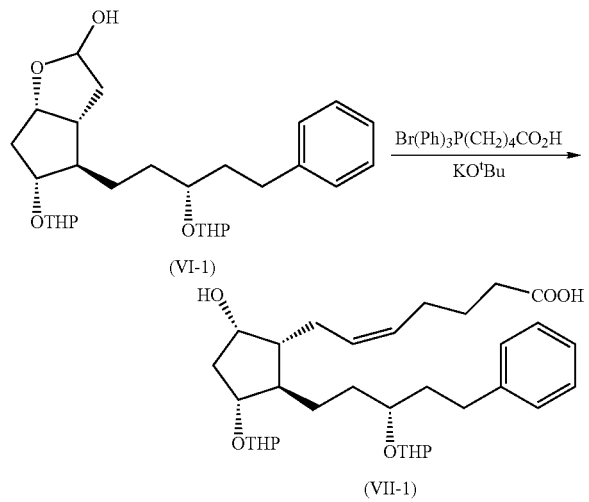

Add 1.93 g 4-carboxybutyl triphenylphosphonium bromide and 15 ml THF into a 25 ml three-necked reaction bottle, decrease the temperature to 0~10° C., then add 1.46 g potassium tetra-butoxide, obtain orange red ylide, stir for 30 minutes, add compound (VI-1) and THF mixture solution (dissolve 0.9 g compound (V-1) into 5 ml THF), react for 1.0 hour, extracted with 10 ml NaHCO₃ and 20 ml ethyl acetate, setting for layers show up, obtain the upper layer, dry with 5 g Na₂SO₄, then filter Na₂SO₄, concentrated the filtrate for 0.9 g yellow oil residue then direct proceed next procedure.

EXAMPLE 10

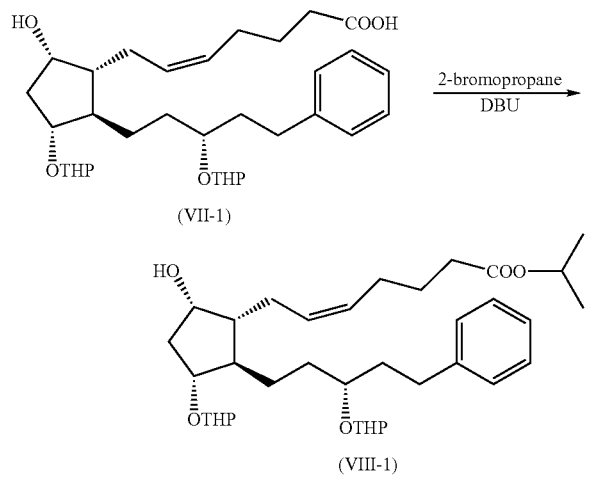

dissolve 39 g compound (VII-1) crude product into 240 ml acetone, add 5.7 g 1,8-diazabicyclo(5.4.0)undec-7-ene (DBU) in temperature 20~25° C., stir for 10 minutes, then add 45 g 2-bromopropane, stir for 12 hours, analysis with TLC, waiting for reaction completed, adjusting by 32% HCl for PH=2.0~6.0, add 100 ml water, extracted with 500 ml ethyl acetate, setting for layers show up, obtain the upper layer then concentrating for 50 g yellow oil residue.

EXAMPLE 11

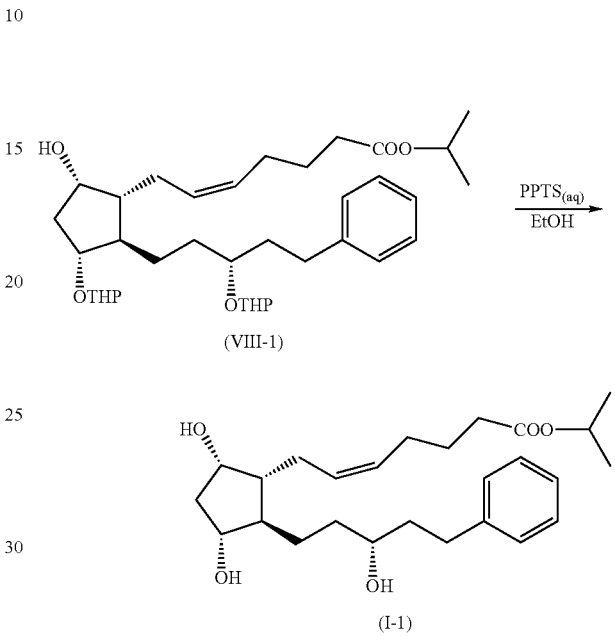

Dissolve 50 g compound (VIII-1) into 250 ml ethanol, add 5 g PPTS in 20~25° C. then heating to 50° C., stir for 3 hours, testing with TLC, wait for reaction complete, replace ethanol by 500 ml ethyl acetate, extracted with 100 ml water and 200 ml ethyl acetate, setting for layers show up, obtain the upper layer, then dry with 40 g Na₂SO₄, filter Na₂SO₄, concentrate the filtrate for 23.5 g yellow oil like residue, purified with column chromatography obtain 13.5 g yellow oil residue.

Rf=0.35 (silica gel, EA/Hx=7/3)

$[\alpha]_D^{20}$=+31.82 (C=0.9, Acetonitrile)

¹H NMR(CDCl₃):

δ: 7.26-7.13 (m, 5H), 5.46-5.34 (m, 2H), 4.99-4.94 (m, 1H), 4.12-4.08 (m, 1H), 3.95-3.92 (m, 1H), 3.63-3.61 (m, 1H), 2.79-2.77 (m, 1H), 2.65-2.62 (m, 1H), 1.90-1.30 (m, 12H), 1.25-1.20(d, 6H)

¹³C NMR(CDCl₃):

δ: 173.50, 142.09, 129.48, 129.34, 128.35, 125.75, 78.66, 74.54, 71.26, 67.64, 52.71, 51.79, 42.45, 38.99, 35.73, 34.02, 32.07, 29.63, 26.82, 26.58, 24.89, 21.78,

MS:m/z=455(M+Na)

From the foregoing description, one skilled in the art can easily ascertain the essential characteristics of this invention, and without departing from the scope thereof, one can make various changes and modifications of the invention to adapt it to various usages and conditions. Thus, other embodiments are also within the claims.

What is claimed is:

1. A method for preparing a compound having a formula (II-b):

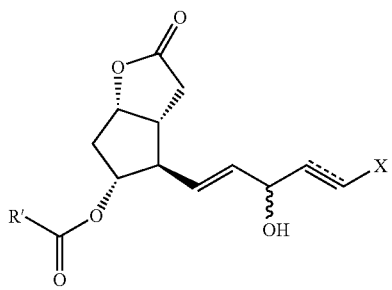

(II-b)

wherein
R' is an aryl group with 0 to 3 substituted groups, wherein said substituted groups are selected from the groups consisting of halogen atom, $C_1$-$C_6$ alkyl, and $C_6$-$C_{10}$ aryl group;

X is $C_1$-$C_6$ alkyl, thiazol, imidazole, pyrrolidine, thiophene, oxazole or a phenyl group with 0 to 3 substituted groups, wherein said substituted groups are selected from the groups consisting of $C_1$-$C_5$ alkyl, $C_1$-$C_4$ alkoxy, trifluoromethyl group, $C_1$-$C_3$ aliphatic acylamino group, nitro group, halogen atom, and phenyl group; and ≡≡≡ is a triple bond or a double bond in the cis or trans position; comprising the following steps:

(a) reacting a Protected-Corey aldehyde as shown below,

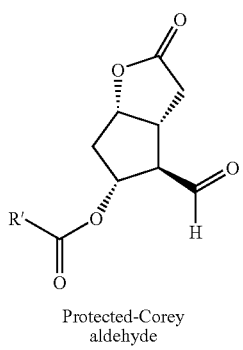

Protected-Corey aldehyde wherein R' is defined as above; with a Phosphonate compound as shown below,

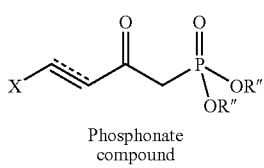

Phosphonate compound wherein R" is $C_1$-$C_6$ alkyl; X and ≡≡≡ are defined as above; to form the following formula (II-a) compound:

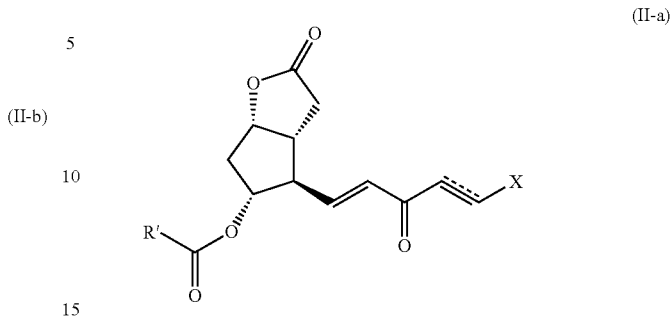

(II-a)

wherein R', X and ≡≡≡ are defined as above; and (b) reducing the formula (II-a) compound to form the formula (II-b) compound

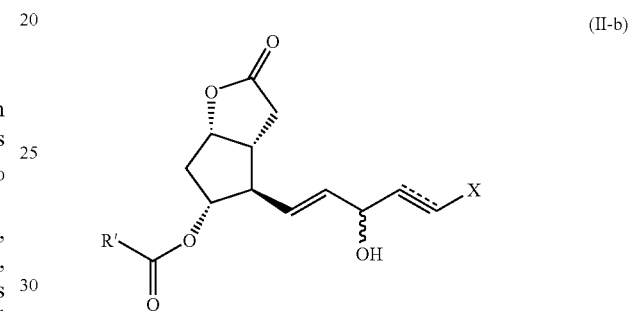

(II-b)

wherein R', X and ≡≡≡ are defined as above.

2. The method of claim 1, further comprising the following steps:

(c) separating the formula (II-b) compound to obtain the following formula (S)-(II-b) compound

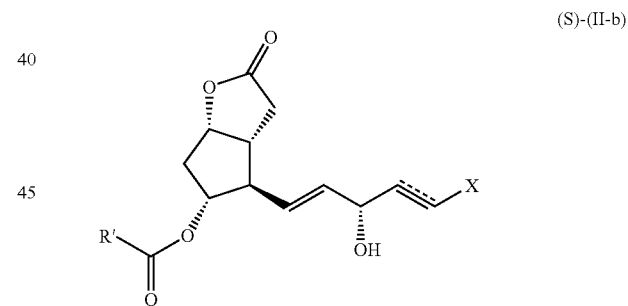

(S)-(II-b)

wherein R', X and ≡≡≡ are defined as claim 1;

(d) hydrogenating the formula (S)-(II-b) compound to form the following formula (III) compound,

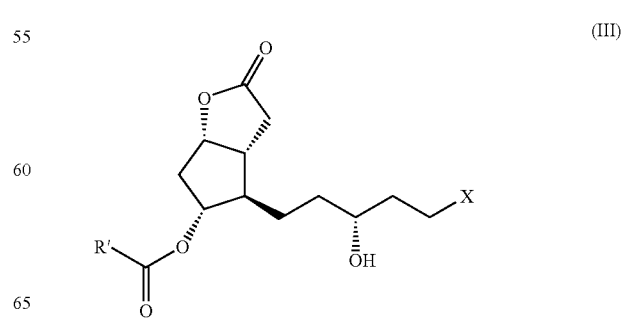

(III)

wherein R' and X and are defined as claim 1;

(e) deprotecting the formula (III) compound to form the following formula (IV) compound

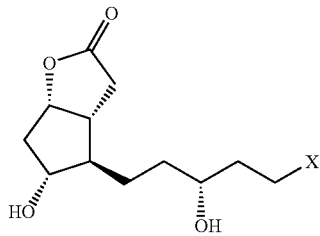
(IV)

wherein X is defined as claim 1; and (f) reacting the formula (IV) compound with a protection reagent to form the following formula (V) compound

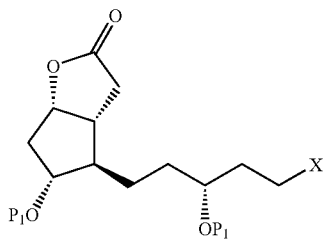
(V)

wherein $P_1$ is a hydroxy-protecting group, said hydroxy-protecting group is selected from the group consisting of N,N'-Bis(trimethylsilyl)urea, trimethylsilyl, triethylsilyl, tbutyldimethylsiyl, t-butyldiphenylsilyl, phenyldimethylsilyl, or tetrahydrofuranyl; X is defined as claim 1;

(g) reducing the formula (V) compound to obtain the following formula (VI) compound

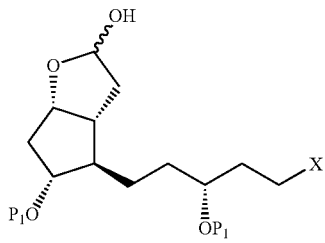
(VI)

wherein $P_1$ is defined as above; and X is defined as claim 1;

(h) reacting the formula (VI) compound with the following compound

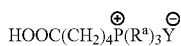

wherein $R^a$ is $C_1$-$C_6$ alkyl or $C_6$-$C_{10}$ aryl group; Y is fluoro, chloro bromo or iodo; to form the following formula (VII) compound

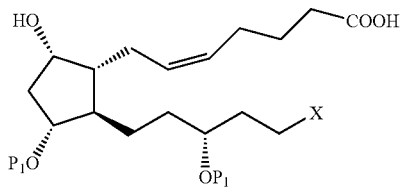
(VII)

wherein X and $P_1$ are defined as above;

(i) reacting the formula (VII) compound with the following compound

R—Z wherein R is defined the same as above claim 1; Z is halogen, sulphate, mesyl, or tosyl: to form the following formula (VIII) compound

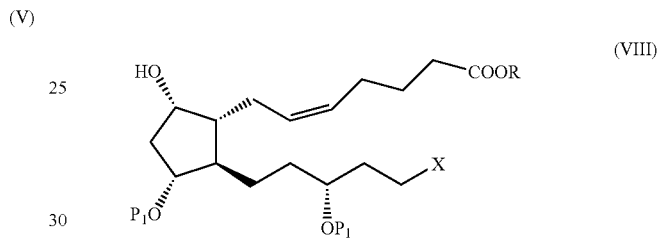
(VIII)

wherein $P_1$ is defined as above; and (j) deprotecting the formula (VIII) compound to form a compound of formula (I)

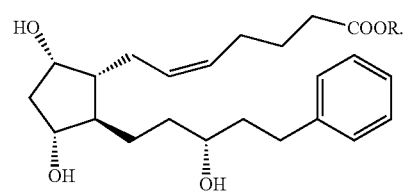
(I)

3. The method of claim 1, further comprising the following steps:

(c) separating the formula (II-b) compound to obtain the following formula (S)-(II-b) compound

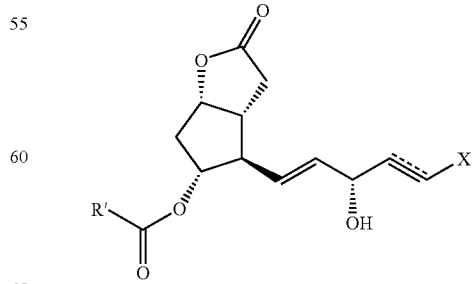
(S)-(II-b)

wherein R', X and ===== are defined as claim 1;

(k) deprotecting the formula (S)-(II-b) compound to form the following formula (S)-(II-c) compound

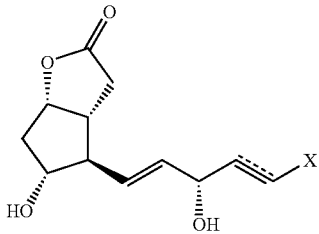

(S)-(II-c)

wherein X and ═══ are defined as claim 1;

(d)' hydrogenating the formula (S)-(II-c) compound to form the following formula (IV) compound

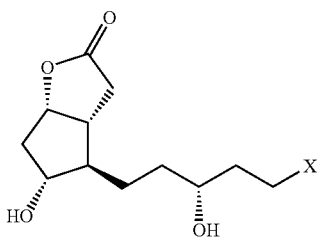

(IV)

wherein X is defined as claim 1;

(f) reacting the formula (IV) compound with a protecting reagent to form the following formula (V) compound

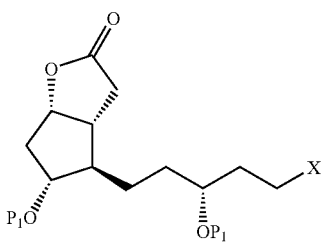

(V)

wherein $P_1$ is defined as claim 2; and X is defined as claim 1;

(g) reducing the formula (V) compound to obtain the following formula (VI) compound

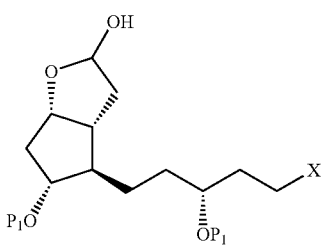

(VI)

wherein $P_1$ is defined as above; and X is defined as claim 1;

(h) reacting the formula (VI) compound with the following compound

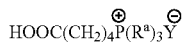

wherein $R^a$ is $C_1$-$C_6$ alkyl or $C_6$-$C_{10}$ aryl group; Y is fluoro, chloro, bromo or iodo; to form the following formula (VII) compound

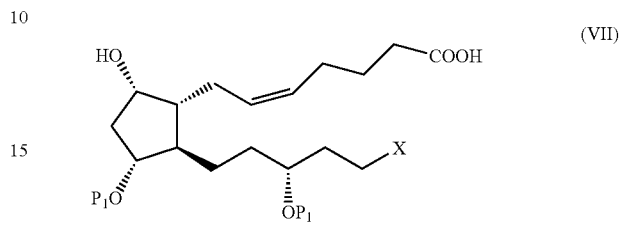

(VII)

wherein X and $P_1$ are defined as above;

(i) reacting the formula (VII) compound with the following compound

wherein R is defined as claim 1; Z is halogen, sulphate, mesyl, or tosyl; to form the following formula (VIII) compound

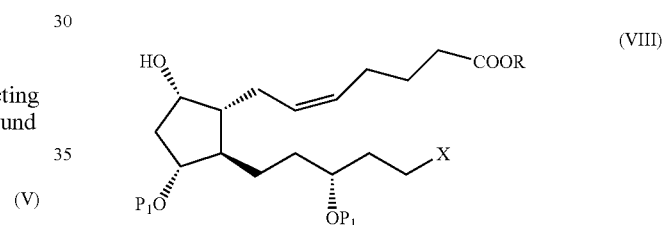

(VIII)

wherein $P_1$, X and R is defined as above; and (j) deprotecting the formula (VIII) compound to form the formula (I) compound.

4. The method of claim 2, wherein said R' is $C_6$-$C_{10}$ aryl group.

5. The method of claim 2, wherein said R' is a aryl group with 1 to 3 substituted groups, wherein said substituted groups are selected from the groups consisting of halogen atom and phenyl groups.

6. The method of claim 2, wherein said R' is a phenyl group.

7. The method of claim 2, wherein said X is a phenyl group with 0 to 3 substituted groups, wherein said substituted groups are selected from the groups consisting of $C_1$-$C_5$ alkyl, $C_1$-$C_4$ alkoxy, trifluoromethyl group, $C_1$-$C_3$ aliphatic acylamino group, nitro group, halogen atom, and phenyl group.

8. The method of claim 2, wherein said X is a phenyl group.

9. The method of claim 2, wherein said X is a phenyl group and said R' is a phenyl group.

10. The method of claim 2, wherein said R is isopropyl group.

11. The method of claim 2, wherein said R is an isopropyl group and X is a phenyl group.

12. The method of claim 3, wherein said R' is $C_6$-$C_{10}$ aryl group.

13. The method of claim 3, wherein said R' is a aryl group with 1 to 3 substituted groups, wherein said substituted groups are selected from the groups consisting of halogen atom and phenyl group.

14. The method of claim 3, wherein said R' is a phenyl group.

15. The method of claim 3, wherein said X is a phenyl group with 0 to 3 substituted groups, wherein said substituted groups are selected from the groups consisting of $C_1$-$C_5$alkyl, $C_1$-$C_4$ alkoxy, trifluoromethyl group, $C_1$-$C_3$aliphatic acylamino group, nitro group, halogen atom, and phenyl group.

16. The method of claim 3, wherein said X is a phenyl group.

17. The method of claim 3, wherein said X is a phenyl group and said R' is a phenyl group.

18. The method of claim 3, wherein said R is isopropyl group.

19. The method of claim 3, wherein said R is an isopropyl group and X is a phenyl group.

* * * * *